United States Patent [19]

Schlosser et al.

[11] Patent Number: 4,745,213

[45] Date of Patent: May 17, 1988

[54] METHOD OF PREPARING ESTERS OF ACRYLIC ACID AND METHACRYLIC ACID BY TRANSESTERIFICATION

[75] Inventors: Fritz Schlosser, Darmstadt; Peter J. Arndt, Seeheim-Jugenheim; Manfred Mueller, Rossdorf; Lothar Janssen, Breuberg, all of Fed. Rep. of Germany

[73] Assignee: Röhm GmbH Chemische Fabrik, Darmstadt, Fed. Rep. of Germany

[21] Appl. No.: 745,486

[22] Filed: Jun. 17, 1985

[30] Foreign Application Priority Data

Jun. 26, 1984 [DE] Fed. Rep. of Germany ....... 3423441

[51] Int. Cl.$^4$ .............................................. C07C 67/02
[52] U.S. Cl. ..................................................... 560/217
[58] Field of Search ......................................... 560/217

[56] References Cited

U.S. PATENT DOCUMENTS 2,138,763 11/1938 Graves .
2,891,990 6/1959 Mulvany et al. ..................... 560/217
2,891,991 6/1959 Stewart et al. ...................... 560/217
3,784,578 1/1974 Swodenk et al. ................... 560/217

FOREIGN PATENT DOCUMENTS 1180527 2/1960 Fed. Rep. of Germany .
2744641 4/1979 Fed. Rep. of Germany .

OTHER PUBLICATIONS

Kirk-Othmer *Encyclopedia of Chemical Technology*, vol. 8, 2nd ed. (1966), pp. 356–362.
Hamamoto, Yoshito et al., *Chemical Abstracts*, vol. 84, #136,271f (1976).
Chemical Abstracts, 43:5036 a,b,c.
Chemical Abstracts, 94:121292w, Mitsui Toatsu Chemicals, Inc.
Chemical Abstracts, 94:121290u, Daicel Chemical Industries, Ltd.
Chemical Abstracts, 91:40095v, Nitto Chemical Industry Co., Ltd.
Chemical Abstracts, 84:136271f, Kyowa Gas Chemical Industry, Co., Ltd.
Chemical Abstracts, 95:7026h, Mitsui Toatsu Chemicals, Inc.
"Synthesis of Acrylic Esters by Transesterification", (1967), J. K. Haken, pp. 3–4.

*Primary Examiner*—Donald B. Moyer
*Assistant Examiner*—L. Hendriksen
*Attorney, Agent, or Firm*—Oblon, Fisher, Spivak, McClelland & Maier

[57] ABSTRACT

A method of preparing an ester of (meth)acrylic acid by transesterification with an alcohol, comprising, reacting a (meth)acrylic acid ester formed from an alcohol of 1 to 4 carbon atoms with a transesterifying alcohol, which is not a polybasic alcohol and which is different from the alcohol portion of said (meth)acrylic acid ester, in the presence of a catalyst system comprised of compounds A+B, wherein compound A is $Li_nY$, wherein Y is a halide, chlorate, carbonate, carboxylate of 1 to 6 carbon atoms, an alkoxide of 1 to 4 carbon atoms, hydroxide or oxide, and n is 1 or 2, depending on the valence of Y; and compound B is $CaX_q$, wherein X is oxide or chloride and q is 1 or 2, depending on the valence of X, with the provision that at least one of the two anionic components Y and X is oxygen-containing.

17 Claims, No Drawings

METHOD OF PREPARING ESTERS OF ACRYLIC ACID AND METHACRYLIC ACID BY TRANSESTERIFICATION

BACKGROUND OF THE INVENTION

1. Field of the Invention

The present invention relates to a method of preparing specific esters of acrylic acid and methacrylic acid (said acids hereinafter designated collectively as "(meth)acrylic acid"). More particularly, the invention relates to esters of higher alcohols and of substituted alcohols other than polyhydric alcohols, said method starting with esters of acrylic and/or methacrylic acid with alcohols having 1-4 carbon atoms, which esters are available from large scale industrial sources, and said method employing metal compounds as catalysts.

2. Discussion of the Background

The catalytic action of inorganic bases in many transesterification reactions is well known (Swiss Pat. No. 239,750). This base-catalyzed reaction is employed advantageously to prepare higher (meth)acrylic acid esters or basic esters from methyl and/or ethyl esters of (meth)acrylic acid (Ger. As 11 80 527; U.S. Pat. No. 2,138,763; G. D. Graves and M. B. Horn in "Acrylic Resins", Reinhold Publ. Corp., N.Y., 1960). It is clear from the literature that effort in the art has been concentrated on solving specific problems of the application of particular catalysts.

In one known prior technique of transesterification, methyl methacrylate is reacted with tetraethylene glycol in benzene in the presence of sodium hydride as described in JACS, 77, 194 (1955). The methanol formed was removed by distillation as a benzene-methanol azeotrope.

The transesterification reaction of methyl acrylate and/or methyl methacrylate with dialkylaminoalkanol in the presence of calcium hydroxide or calcium oxide is disclosed in Japanese Laid Open Application No. 75-142,513 (see CA, 84, 136271f).

Catalytic acceleration of the transesterification of methyl methacrylate with, e.g., 2-ethylhexanol, by a lithium compound such as lithium hydride, alkyllithium, phenyllithium, lithium aluminum hydride, lithium borohydride or an alkoxide of lithium borohydride, lithium salts of organic or inorganic acids, lithium acetylacetonate, lithium oxide, or lithium metal, is disclosed in Jap. OS No. 79-41,815 (CA, 91, 40095v). Particular interest has been shown in the transesterification of lower esters of (meth)acrylic acid with glycidol to form glycidyl esters. The transesterification of methyl methacrylate with glycidol in the presence of alkali hydroxides, or alkali carbonates, -sulfides, -polysulfides, or -thiosulfates, lithium halides, or sodium-, potassium-, rubidium-, or cesium iodides is the subject of Japanese Laid Open Application No. 80-94,378 (CA, 94, 121290u).

Transesterification of methyl (meth)acrylate with glycidol in the presence of alkali halides, particularly lithium chloride, to yield glycidyl (meth)acrylate, is described in Japanese Laid Open Application No. 80-105,676 (CA, 95, 121292W), while Japanese Laid Open Application No. 80-127380 (CA, 95, 7026h) discloses the transesterification of lower esters of other organic carboxylic acids with glycidol in the presence of alkali halides, particularly sodium bromide.

In the art there is a recognized need for, in addition to (meth)acrylic acid esters such as methyl methacrylate, which are produced on a large industrial scale, additional specialty esters which, e.g., enable modification of the polymer properties or the production of special polymer systems (see H. Rauch-Puntigam and Th. Voelker, "Acryl- und Methacrylverbindungen", Springer-Verlag, 1967)), J. Brandrup and E. H. Immergut Ed., "Polymer Handbook" 2nd Ed. J. Wiley & Sons 1975.)

The progress made by those skilled in the art toward solving the specific problems of preparing special esters of (meth)acrylic acid has been in the area of devising specific transesterification catalysts. In the interest of a maximally integrated technology, however, there is also a need for a method, which should be generally applicable, to improve product quality and yield without having to make any ecological or economic concessions. Two other factors beside ecology and cost which add to the difficulty of the problem are the risk of polymerization (when esters of polymerizable acids are employed) under the conditions of the reaction and/or subsequent processing, and the side reactions which occur. Further, ester interchange with certain alcohols present special problems.

A particular aspect of the above-stated problem is to influence the transesterification of esters of carboxylic acids such as (meth)acrylic acid, which acids can polymerize by radical polymerization, said interchanges involving specific alcohols, such that one maximizes the degree of the transesterification, i.e. achieves high yields with maximum selectivity.

The state of the art gives no indication or hint of the fact that a catalyst system comprised of different components, which are individually relatively inactive, can exhibit a synergistic action in transesterification reactions according to the previously stated underlying problem of the invention.

SUMMARY OF THE INVENTION

Accordingly, one object of the present invention is to provide a methodology of producing (meth)acrylic acid esters by transesterification which produces a (meth)acrylic acid ester simply and in high yield.

Briefly, this object and other objects of the present invention as hereinafter will become more readily apparent can be obtained by a process for producing a (meth)acrylic acid ester in a transesterification reaction by reacting a (meth)acrylic acid ester formed from an alcohol of 1 to 4 carbon atoms with a transesterifying alcohol, which is not a polybasic alcohol, and which is different from the alcohol portion of said (meth)acrylic acid ester in the presence of a catalyst system comprised of compounds A+B, wherein compound A is $Li_nY$, wherein Y is a halide, chlorate, carbonate, carboxylate of 1 to 6 carbon atoms, an alkoxide of 1 to 4 carbon atoms, hydroxide or oxide, and n is 1 or 2 depending on the valence of Y; and compound B is $CaX_q$, wherein X is oxide or chloride and q is 1 or 2 depending on the valence of X, with the provision that at least one of the two anionic components Y and X is oxygen-containing.

DETAILED DESCRIPTION OF THE PREFERRED EMBODIMENTS

The starting material for the transesterification reaction of the present invention advantageously comprises esters of (meth)acrylic acid with alcohols having 1-4 carbon atoms, which esters are industrially in good supply, particularly the esters with alcohols having 1-2 carbon atoms, i.e. the ethyl ester and particularly the methyl ester.

The alcohols used in the transesterification reaction, which alcohols differ from the alcohols from which the starting esters are derived, can be represented generally by Formula I:

ROH (I), wherein R is
(a) a linear alkyl group with 2–30 carbon atoms,
(b) a branched alkyl group with 3–40 carbon atoms,
(c) a cyclic alkyl group with 5–30 carbon atoms,
(d) an arylalkyl group with 7–18 carbon atoms,
(e) a heterocyclic group Z,
(f) an alkyl group with 2–12 carbon atoms with one or more amine moieties "A" in the molecule; and
(g) an alkyl group with 1–18 carbon atoms and containing a functional group G which is different from the substitutions defined in (e) or (f);
wherewith the groups R as defined in (a)–(g) may have in addition one or more chemically inert substituents Q, which differ from the substituents mentioned in (e)–(g).

The said chemically inert substituents Q shall be understood to be groups, other than hydrocarbon groups, which are not polymerizable by radical polymerization under the conditions of the transesterification, and in particular the likes of halogen such as F, Cl, and Br and/or an ether group of the formula: $-OR_1$, wherein $R_1$ ia an alkyl group with 1–18 carbon atoms, preferably 1–6 carbon atoms, a phenyl group, or a group of the formula:

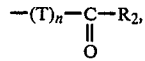

wherein $R_2$ is (a) an alkyl group with 1–30 carbon atoms, (b) a group $-OR_1'$, wherein $R_1'$ is the same as defined for $R_1$, (c) a group of the formula $-NR_3R_4$, wherein $R_3$ and $R_4$ are mutually independently hydrogen or phenyl or an alkyl group with 1–6 carbon atoms, or groups $R_3$ and $R_4$, together with nitrogen(s) atoms and possibly other hetero atoms comprise a 5- or 6- membered heterocyclic ring, T is an oxygen atom or a group $-NR_5$, where $R_5$ is hydrogen or an alkyl group of 1–6 carbon atoms, and n is 0 or 1.

The alcohols ROH having linear alkyl groups R, (alternative (a) above (Formula I)) shall be understood to be linear alcohols which are primary or secondary alcohols, particularly alcohols having 3 or more carbon atoms, particularly alcohols having up to 24 carbon atoms.

The alcohols ROH having branched alkyl groups R, (alternative (b) above (Formula I)) shall be understood to include, in particular, primary and secondary branched alcohols, especially those having 3–28 carbon atoms. Particularly important with respect to the alcohols ROH of the type (a) and (b) above are the relevant secondary alcohols, e.g., isopropanol and 2-butanol.

Also of industrial interest are transesterification reactions with linear alcohols which are primary higher alcohols such as are obtained from large scale processes, said alcohols having average numbers of carbon atoms between 8 and 18. Of these, one might mention, e.g., the linear primary alcohols recovered from hydroformylation reactions, e.g., the alcohols marketed under the trade name Dobanol ® of the firm Shell Chemie, and the alcohols produced in the Ziegler process involving hydrolysis of aluminum alkoxides and having 4–20 carbon atoms, having the tradename Alfol ® of the firm Condea, of Hamburg, and fatty alcohols and fatty alcohol fractions having the tradename Lorol ® of the firm Henkel KG. In particular, one might mention alcohols having 10–24 carbon atoms, especially those having 18–20 carbon atoms, and as individual examples decyl, undecyl, lauryl, oleyl, and octadecyl alcohol. Further, one might mention alcohols having one or more substituents Q as defined supra of the likes of fluorinated alcohols; chlorinated alcohols such as 2,3-dichloropropanol; ether alcohols such as diethylene glycol monoethyl ether, n-butyl diglycol, beta-methoxyethanol, beta-ethoxy glycol; acylated alcohols such as beta-acetoxyethanol, beta-choloracetoxyethanol, and beta-hydroxypropanoic acid ethyl ester; and amide group containing alcohols such as N-hydroxyethyl-N-methyl fatty acid amides, e.g., N-hydroxyethyl-N-methylcocinamide.

With regard to the alcohols ROH which contain cyclic alkyl groups, (alternative (c) above), included are industrially available alcohols such as cyclohexanol, cyclooctanol, and also alkylated cyclic alcohols such as 3,3,5-trimethylcyclohexanol, and terpenoid alcohols and their derivatives such as isoborneol. The alicyclic group may also have the hydroxyl groups on an alkyl substituent. With regard to the alcohols ROH which contain arylalkyl substituents (alternative (d) above), included are arylalkanols such as benzyl alcohol, phenylethanol, and 3-phenyl-1-propanol. With regard to the alcohols ROH which contain heterocyclic substituents (alternative (e) above), included are heterocyclic alcohols, which may have the hydroxyl group on an alkyl substituent of the heterocyclic system and/or on the heterocyclic system itself. The said heterocyclic ring system shall be understood to be particularly a 3-, 5-, or 6-membered heterocyclic ring which generally contains as the hetero atom(s), nitrogen(s) and/or oxygen(s) and/or sulfur(s) and which may have alkyl group substituents having 1–6 carbon atoms. Exemplary heterocyclic alcohols include imidazole derivatives such as 2-(1-imidazolyl)ethanol, 2-(2-methyl-$\Delta^2$-1-imidazolinyl)ethanol, alcohol derivatives of 2,3-dihydro-4H-pyran, 2,2-dimethyl-4-hydroxymethyl-1,3-dioxolan, N-(beta-hydroxyethyl)morpholine, furfuryl alcohol, tetrahydrofurfuryl alcohol, glycidine, hydroxymethyldioxolan, and 2-ethyl-5-(beta-hydroxyethyl)dioxane.

With regard to the alcohols ROH which contain aminated alkyl groups (alternative (f) above), particularly included are alcohols of formula HO-R'-NR$_3$'R$_4$', wherein R' is a possibly branched hydrocarbon chain with 2–30, preferably 2–12 carbon atoms or a possibly substituted cyclic group with 5–20 carbon atoms, and $R_3'$ and $R_4'$ have the same definition as $R_3$ and $R_4$ supra. Aminated alcohols include dimethylamine- and diethylamine-substituted ethanols, -propanols, -butanols, -pentanols, and -hexanols.

With regard to the alcohols ROH which contain "G"-substituted alkyl groups (alternative (g) above), chiefly include alcohols of the formula HOR", where R" is a possibly branched hydrocarbon group with 1–30, preferably 1–12 carbon atoms or is a possibly alkyl-substituted and/or halogen-substituted cyclic group with 5–20 Carbon atoms, containing as the functional group G one or more carbon single, double, or triple bonds, or a nitrile, ureido, vinyl ether, or vinylcarboxylate group. Included are alcohols such as allyl alcohol and vinyloxyethanol.

From, the point of view of obtaining the results of the present invention, the subject catalyst system (A+B) is not very suitable, however, for catalyzing transesterification involving tertiary alcohols or phenolic OH groups as the replacing moiety.

The catalyst system of the present invention (A+B) is advantageously employed in catalytic amounts, generally 0.01 to 10 wt. %, preferably 0.2 to 5 wt. %, based on the amount of the substituting alcohol employed. Accordingly, the amount of component A in the catalyst system A+B is 5-95 wt. %, preferably 10-90 wt. %, and the amount of component B is 95-5 wt. %, preferably 90-10 wt. %; particularly, B may be present in gravimetric excess over A, e.g. in an amount of twice the amount of A.

With respect to standard amounts of the catalyst components, from 0.2-5 wt. %, preferably 1-3 wt. %, of B along with 0.2-2, preferably 0.5-2 wt. % of A may be employed (based on the amount of the substituting alcohol), and particularly under the condition that the weight ratio of B:A is 2:1. Advantageously, the catalysts are employed in finely divided form, e.g. as powders or fine crystals. The components A and B may be mixed in advance or may be added individually to the reaction mixture. Examples of A+B catalyst systems include:

Lithium oxide + Calcium oxide,
Lithium hydroxide + Calcium oxide,
Lithium alkoxide + Calcium oxide,
Lithium carbonate + Calcium oxide,
Lithium acetate + Calcium oxide,
Lithium fluoride + Calcium oxide,
Lithium chloride + Calcium oxide,
Lithium bromide + Calcium oxide,
Lithium iodide + Calcium oxide,
Lithium chlorate + Calcium oxide, and
Lithium methoxide + Calcium chloride.

With regard to alkoxide compounds. Particularly useful are the methoxides, ethoxides, and t-butoxides.

It is advantageous to employ an excess of the (meth)acrylic ester in the reaction over the amount stoichiometrically required for transesterification. In general, the (meth)acrylic ester is present in 1.5- to 3-fold excess amount, particularly a 2.5-fold excess amount. In general it is recommended that when scaling up the system beyond laboratory scale the amount of excess of the initial (meth)acrylic ester should be reduced.

The use of a solvent along with the other components of the reaction mixture is not generally necessary. However, it is possible to use inert (non-radical-forming) solvents including hydrocarbons such as toluene, cyclohexane, n-hexane, and n-heptane. A stabilizer (radical scavenger) is recommended to inhibit polymerization of the (meth)acrylic esters. For this purpose the usual stabilizers may be used, which include hydroquinone compounds, thio compounds, and amines, in the usual amounts (50-5000 ppm). (See H. Rauch-Puntigam and Th. Voelker, "Acryl- und Methacrylverbindungen", Springer-Verlag, p. 165 (1967)).

Advantageously, the reaction temperature is above room temperature, preferably in the range of 60°-120° C. In general the overall reaction times are in the range 5-20 hr, preferably 6-12 hr. As a guideline value (standard estimate) for the duration of the alcoholysis proper, in many cases one may assume 3+ or −1 hr, and for the remainder of the time to completion about an additional 2-3 hrs. It must be borne in mind that the amounts of the components in the reaction mixture play a role. If methyl methacrylate or methyl acrylate is employed as the preferred starting ester, advantageously the methanol formed in the transesterification may be drawn off of the reaction medium in an azeotropic mixture with the (meth)acrylic acid ester at 65°-75° C.

The reaction may be carried out as follows. The alcohol is charged into a suitable reaction vessel with the excess of the (meth)acrylic acid ester and the stabilizer. The catalyst may be added as a mixture or separately. Thus, e.g., a lithium alcoholate in a suitable solvent, e.g., lithium methoxide in methanol, may be added. In general, it is recommended that the addition of the catalyst components be in finely divided form, e.g. if not in solution, then in powdered or granular form. In any event, the initial degree of dispersion of the catalyst does not seem to be critical.

The reaction mixture is brought to the reaction temperature under agitation. When methyl methacrylate is used as the starting ester, for example, the mixture is heated to boiling. The resulting methanol is first advantageously drawn off along with unreacted ester at a distillation head temperature of up to 70° C. At a head temperature of up to c. 98° C. the residual methanol is drawn off along with some more of the residual unconverted ester. Finally, advantageously, the remaining residual unconverted ester is removed by distillation at reduced pressure, with a maximum bottom temperature of 150° C.

Further processing continues in the known fashion; e.g., it has proved successful to add fuller's earth or activated charcoal to the raw ester product, to allow the mixture to settle briefly, and then filter the mixture in a settling filter or pressure filter.

The yield of the desired transesterification product is quite high by the present method, and is usually on the order of >90%. Particularly noteworthy is the extremely small proportion of addition products to the vinyl double bond of the product ester, and of other byproducts.

Having generally described this invention, a further understanding can be obtained by reference to certain specific examples which are provided herein for purpose of illustration only and are not intended to be limiting unless otherwise specified.

EXAMPLES 1 to 12

Apparatus

A 2-liter round bottom flask is equipped with a mushroom-shaped heating mantle, sword-shaped stirrer, thermometer, air inlet tube, metallized column packing comprised of glass raschig rings 4×4 mm, automatic gas-phase separator, condenser, adapter, and receiver.

Procedure

The alcohol (ROH) and methyl methacrylate were charged into the flask in the mole ratio 1:2.5, along with 200 ppm hydroquinone monomethyl ether, and with pulverized LiCl/CaO in the weight ratio 1:2. The reaction mixture was heated to boiling, with stirring and air was introduced. The methanol which formed in the alcoholysis was continuously drawn off until no more methanol formed. Then, without limiting the head temperature, the excess methyl methacrylate was distilled off until the bottom temperature reached 135° C. The residual mixture was then degassed at 110° C. and 10 mbar. The raw product ester was checked by gc. The results are given in the following Table.

TABLE OF RESULTS

| Example | Alcohol ROH | LiCl/CaO Catalyst System in wt % based on the alcohol | Conversion based on the amount of alcohol (ROH) | Yield of transesterification product, based on ROH converted |
|---|---|---|---|---|
| 1 | Butanol-2 | 1.1/2.2 | 56.5% | 100% |
| 2 | Cyclohexanol-1 | 0.9/1.8 | 99.2% | 100% |
| 3 | Benzylalcohol | 0.8/1.7 | 100% | 92.7% |
| 4 | 2-Ethyl-hexanol | 0.7/1.5 | 100% | 92.1% |
| 5 | ALFOL 10 ® | 0.65/1.3 | 100% | 93.4% |
| 6 | DOBANOL ® - Talgfett-Misch.[1] | 0.55/1.1 | 100% | 83.3% |
| 7 | Tetrahydrofurfuryl-alcohol | 0.85/1.7 | 100% | 83.8% |
| 8 | Allylalcohol | 1.3/2.6 | 97.7% | 95% |
| 9 | Glycidol | 1.1/2.2 | 98.8% | 30.9% |
| 10 | 2-Dimethylaminoethanol | 1.0/2.0 | 99.1% | 88.5% |
| 11 | tert. Butanol | 1.1/2.2 | no conversion | |
| 12 | Phenol | 0.9/1.8 | no conversion | |

[1]DOBANOL ® - Mixture of Dobanol 25L (supplied by Shell), in an amount of 77 wt. %, and tallow fat alcohol with an average number of carbon atoms = 14.2 (Henkel), in the amount of 23 wt. %.

It was found that comparable results could be obtained using the following catalyst systems instead of LiCl+CaO:
Lithium oxide+Calcium oxide, and/or
Lithium hydroxide+Calcium oxide, and/or
Lithium methoxide+Calcium oxide, and/or
Lithium t-butoxide+Calcium oxide, and/or
Lithium acetate+Calcium oxide, and/or
Lithium bromide+Calcium oxide, and/or
Lithium iodide+Calcium oxide, and/or
Lithium chlorate+Calcium oxide, and/or
Lithium methoxide+Calcium chloride.

How now fully described this invention, it will be apparent to one of ordinary skill in the art that many changes and modifications can be made thereto without departing from the spirit or scope of the invention as set forth herein.

What is claimed as new and is intended to be secured by Letters Patent is:

1. A method for preparing an ester of (meth)acrylic acid by trans-esterification with an alcohol, comprising reacting a (meth)acrylic acid ($C_{1-4}$) ester with a trans-esterifying monohydric alcohol haivng a higher molecular weight of higher boiling point than the ($C_{1-4}$) alcohol portion of the said (meth)acrylic acid ($C_{1-4}$) ester, in the presence of a catalyst, where the catalyst is LiCl/CaO or LiBr/CaO or LiI/CaO or mixture thereof, said transesterifying monohydric alcohol being a member selected from the group consisting of all monohydric alcohols other than glycidol.

2. The method of claim 1, comprising using LiCl/CaO.

3. The method of claim 1, comprising using LiBr/CaO.

4. The method of claim 1, comprising using LiI/CaO.

5. The method of claim 1, comprising using a mixture of at least two of the following: LiCl/CaO; LiBr/CaO; LiI/CaO.

6. The method of claim 1, comprising using the catalyst in an amount of 0.01 to 10 wt. % based on the weight of the trans-esterifying alcohol employed.

7. The method of claim 6, comprising using a catalyst containing from 5-95 wt. % of LiCl, LiBr or LiI, and from 95-5% of CaO.

8. The method of claim 1, comprising using a reaction time of from 5-20 hr.

9. The method of claim 8, comprising using a reaction time of from 6-12 hr.

10. The method of claim 1, comprising using an excess of the (meth)acrylic acid ($C_{1-4}$) ester relative to the said trans-esterifying alcohol.

11. The method of claim 10, comprising using a 1.5-fold to 10-fold molar excess of the (meth)acrylic acid ($C_{1-4}$) ester relative to the said transesterifying alcohol.

12. The method of claim 11, comprising using a 2.5-fold molar excess of (meth)acrylic acid ($C_{1-4}$) ester.

13. The method of claim 1, comprising running the trans-esterifying reaction at a temperature above 60° C., and up to 120° C.

14. The method of claim 1, comprising using methyl methacrylate.

15. The method of claim 14, comprising removing methanol formed during the course of the transesterification reaction, said methanol being removed azeotropically together with methyl methacrylate.

16. The method of claim 1, comprising obtaining a trans-esterification product in a yield >90% based on the trans-esterifying alcohol.

17. The method of claim 1, comprising using a trans-esterifying alcohol of the formula ROH; wherein R is:
(a) a linear alkyl group of 2-3 carbon atoms;
(b) a branched alkyl group of 3-40 carbon atoms;
(c) a cyclic alkyl group of 5-30 carbon atoms;
(d) an arylalkyl group of 7-18 carbon atoms;
(e) a heterocyclic group;
(f) an alkyl group of 2-12 carbon atoms having one or two amine moieties; or
(g) a substituted alkyl group of 1-18 carbon atoms.

* * * * *